(12) United States Patent
Abbasi et al.

(10) Patent No.: US 10,045,721 B2
(45) Date of Patent: Aug. 14, 2018

(54) APPARATUS, SYSTEM, AND METHOD FOR AUTOMATIC POWER REDUCTION IN PHOTOPLETHYSMOGRAPHY AND PULSE OXIMETRY SYSTEMS

(71) Applicant: Intel Corporation, Santa Clara, CA (US)

(72) Inventors: Mohammad U. Abbasi, Swindon (GB); Sendill K. Gnanaeswaran, Swindon (GB); Nicholas P. Cowley, Wrouhton (GB)

(73) Assignee: Intel Corporation, Santa Clara, CA (US)

( * ) Notice: Subject to any disclaimer, the term of this patent is extended or adjusted under 35 U.S.C. 154(b) by 47 days.

(21) Appl. No.: 15/085,527

(22) Filed: Mar. 30, 2016

(65) Prior Publication Data
US 2017/0281066 A1  Oct. 5, 2017

(51) Int. Cl.
*A61B 5/1455* (2006.01)
*H03K 5/24* (2006.01)
*A61B 5/00* (2006.01)
*A61B 5/024* (2006.01)

(52) U.S. Cl.
CPC ...... *A61B 5/14551* (2013.01); *A61B 5/02416* (2013.01); *A61B 5/6824* (2013.01); *H03K 5/24* (2013.01); *A61B 2560/0209* (2013.01); *A61B 2560/0223* (2013.01)

(58) Field of Classification Search
CPC ...... H03K 5/24; A61B 5/14551; A61B 5/6824
See application file for complete search history.

(56) References Cited

U.S. PATENT DOCUMENTS

| | | | | |
|---|---|---|---|---|
| 5,645,059 A | * | 7/1997 | Fein | A61B 5/0002 356/41 |
| 5,676,141 A | * | 10/1997 | Hollub | A61B 5/14551 356/41 |
| 5,782,758 A | * | 7/1998 | Ausec | H04L 1/20 600/336 |
| 5,919,134 A | * | 7/1999 | Diab | A61B 5/14551 600/323 |

(Continued)

FOREIGN PATENT DOCUMENTS

| | | |
|---|---|---|
| WO | 2015166990 A1 | 11/2015 |
| WO | 2016000986 A1 | 1/2016 |

OTHER PUBLICATIONS

International Search Report and Written Opinion for International Patent Application No. PCT/US2017/019925, dated May 29, 2017, 17 pages.

*Primary Examiner* — Chanh Nguyen
*Assistant Examiner* — Jonathan G Cooper
(74) *Attorney, Agent, or Firm* — Jordan IP Law, LLC

(57) ABSTRACT

Systems, apparatuses and methods may provide for a transmit circuit including a light source and a receive circuit including a photodetector and a transimpedance amplifier (TIA) coupled to the photodetector. Additionally, a calibration circuit may be coupled to the transmit circuit and the receive circuit, wherein the calibration circuit includes a current controller to set an operational current of the light source to a minimum value that results in a target output voltage of the receive circuit. In one example, the gain of the TIA remains substantially constant during calibration of the receive circuit.

13 Claims, 4 Drawing Sheets

(56) References Cited

U.S. PATENT DOCUMENTS

| | | | |
|---|---|---|---|
| 6,731,967 B1* | 5/2004 | Turcott | A61B 5/0261 600/407 |
| 2005/0187446 A1 | 8/2005 | Nordstrom et al. | |
| 2005/0250997 A1* | 11/2005 | Takeda | A61B 5/14551 600/310 |
| 2006/0009688 A1* | 1/2006 | Lamego | A61B 5/14551 600/323 |
| 2007/0197885 A1* | 8/2007 | Mah | A61B 5/14532 600/310 |
| 2009/0163784 A1 | 6/2009 | Sarpeshkar et al. | |
| 2012/0108928 A1 | 5/2012 | Tverskoy | |
| 2013/0296665 A1* | 11/2013 | Kassim | G01N 21/3151 600/310 |
| 2014/0288435 A1* | 9/2014 | Richards | A61B 5/02427 600/479 |
| 2015/0102209 A1* | 4/2015 | Xu | G01J 1/44 250/214 LS |

* cited by examiner

APPARATUS, SYSTEM, AND METHOD FOR AUTOMATIC POWER REDUCTION IN PHOTOPLETHYSMOGRAPHY AND PULSE OXIMETRY SYSTEMS

TECHNICAL FIELD

Embodiments generally relate to photoplethysmography (PPG) and pulse oximetry (PO) measurements. More particularly, embodiments relate to automatic power reduction in PPG and PO systems.

BACKGROUND

Photoplethysmography (PPG) and pulse oximetry (PO) measurement systems may use a light emitting diode (LED) to illuminate the skin of a subject and a photodetector to capture reflected light from the subject in order to determine heart rate and oxygen saturation of the blood. Conventional approaches may drive the transmitting LED at maximum power, while relying on a central processing unit (CPU) to adjust the gain of programmable amplifiers that amplify analog signals from the photodetector (e.g., to take the programmable amplifiers out of saturation). Such an approach may increase delays and power consumption. For example, the receive path to the CPU may be relatively complex and may include an analog to digital conversion (ADC) stage that introduces considerable delay. Additionally, components such as the CPU, ADC, main crystal oscillator, etc., may consume substantial power.

BRIEF DESCRIPTION OF THE DRAWINGS

The various advantages of the embodiments will become apparent to one skilled in the art by reading the following specification and appended claims, and by referencing the following drawings, in which:

DESCRIPTION OF EMBODIMENTS

Figure 1:
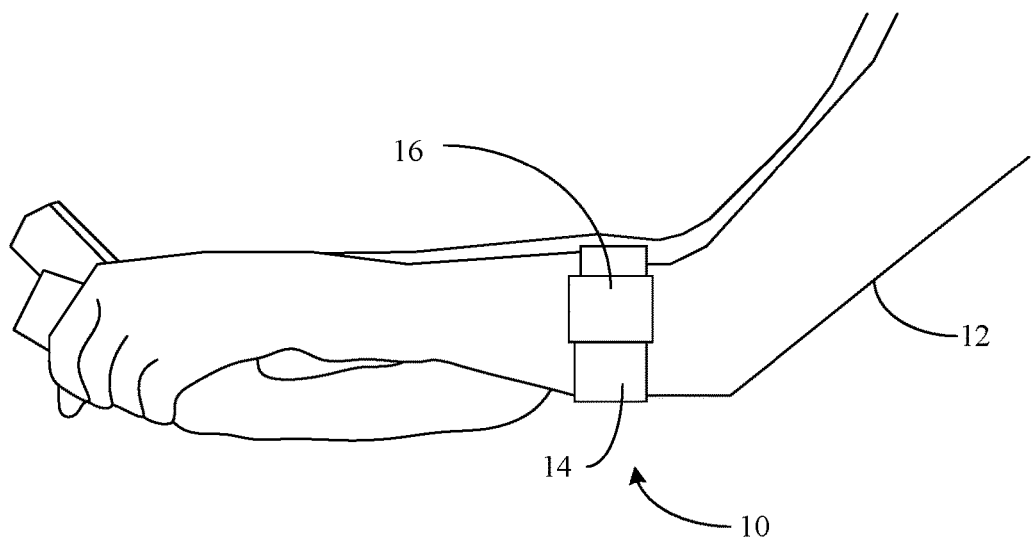
FIG. 1 is an illustration of an example of a health monitor system in a usage environment according to an embodiment.
Figure 2:
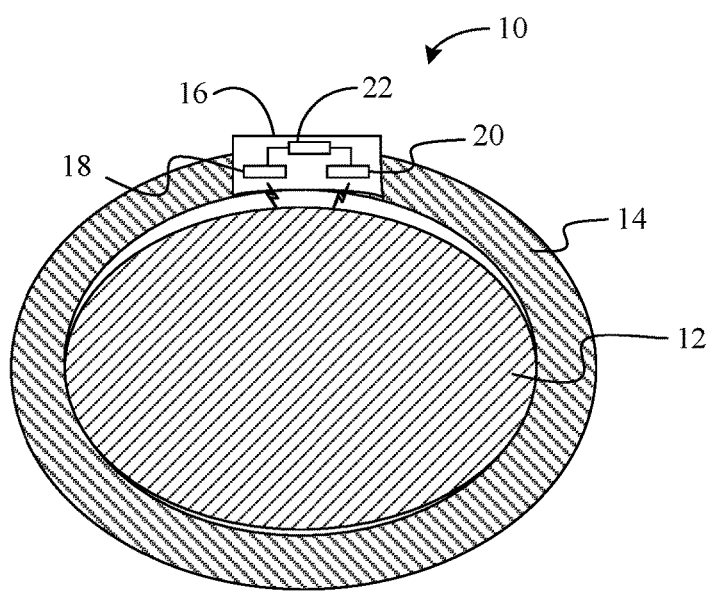
FIG. 2 is a sectional view of the health monitor system shown in FIG. 1 according to an embodiment.

Turning now to FIGS. 1 and 2, a health monitor system 10 is shown in an example usage environment. In the illustrated example, the system 10 is worn on the arm 12 of an individual during an activity such as, for example, exercise. Accordingly, the system 10 may include a housing having a band 14 and an enclosure 16 that define a wearable form factor for the system 10. Other wearable form factors such as, for example, wrist wear, eyewear, headwear, footwear, jewelry, chest straps, etc., may also be used. As best shown in FIG. 2, the system 10 may include a transmit circuit 18, a receive circuit 20 and a calibration circuit 22. The transmit circuit 18 may include a light source (not shown) that directs light toward the arm 12 of the individual, wherein the receive circuit 20 may measure light reflected from the arm 12 of the individual. Because the amount of light detected by the receive circuit 20 may generally be indicative of the amount of blood flow to the skin, the illustrated system 10 may be used to take photoplethysmography (PPG) and/or pulse oximetry (PO) measurements (e.g., monitor heart rate, blood oxygen saturation and other circulatory conditions).

As will be discussed in greater detail, the calibration circuit 22 may set the operational current of the light source in the transmit circuit 18 to a minimum value that results in a target (e.g., relatively low) output voltage of the receive circuit 20. Such an approach may eliminate delays and reduce power consumption. For example, the receive circuit 20 and the calibration circuit 22 need not rely on a central processing unit (CPU) or an analog to digital conversion (ADC) stage that may otherwise introduce considerable delay or increase power consumption.

Figure 3:
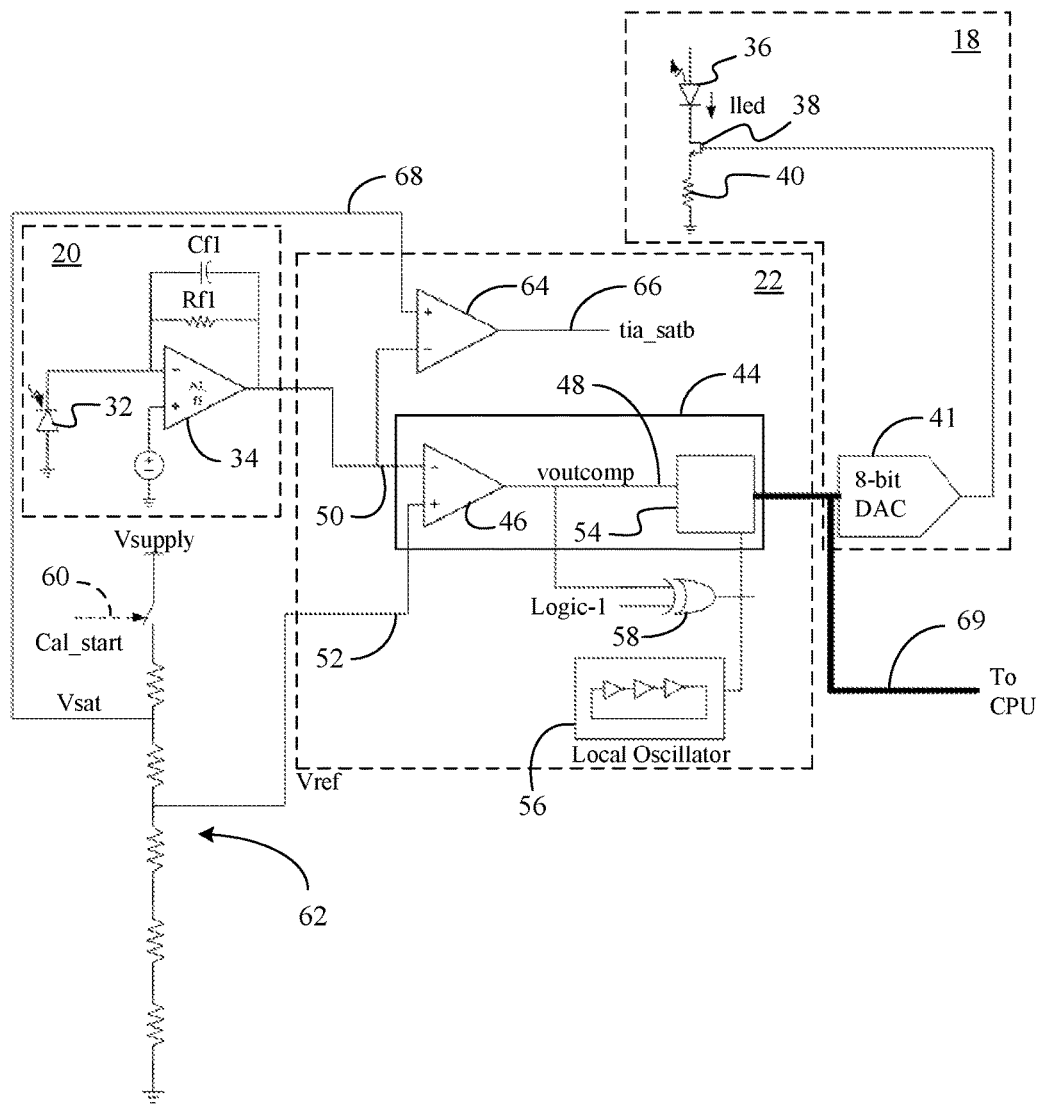
FIG. 3 is a schematic diagram of an example of a transmit and receive circuit calibration phase according to an embodiment.

Turning now to FIG. 3, a transmit and receive circuit calibration phase 42 is shown. The phase 42 may generally be incorporated into a health monitor system such as, for example, the system 10 (FIG. 1), already discussed. In the illustrated example, the calibration circuit 22 includes a current controller 44 to set the operational current of the light source 36 to a minimum value that results in a target output voltage of the receive circuit 20. More particularly, the current controller 44 may include a reference comparator 46 to generate a first comparison signal 48 (e.g., "Voutcomp") based on the difference between a calibration output voltage 50 (e.g., "Vouttia") of the receive circuit 20 and a reference voltage 52 (e.g., "Vref"). The reference voltage 52 may be obtained from a resistor ladder 62. The illustrated current controller 44 also includes a counter 54 (e.g., 8-bit) coupled to the reference comparator 46, wherein the counter 54 generates a counter value based on the first comparison signal 48. In the illustrated example, the transmit circuit 18 also includes a digital to analog converter (DAC) 41 coupled to the switch 38 and the calibration circuit 22, wherein the DAC 41 maintains the operational current of the light source 36 at the minimum value based on the counter value from the counter 54 in the calibration circuit 22. The calibration circuit 22 may also include a local oscillator 56 (e.g., low power clock signal source) coupled to the counter and a logic gate 58 (e.g., exclusive OR/XOR gate) coupled to the reference comparator 46.

During operation of the transmit and receive circuit calibration phase 42, an initiation signal 60 (e.g., "Cal_start") may activate the resistor ladder 62 and turn on the counter 54 with a lowest setting, which may in turn establish a relatively low current setting for the light source 36. Reflected light may be collected by the photodetector 32, wherein the illustrated photodetector 32 sends an analog signal to the TIA 34. The analog signal may have a voltage that is substantially proportional to the amount of reflected light received by the photodetector 32. The illustrated TIA 34, which has a gain that is substantially constant during the phase 42, generates the calibration output voltage 50. The reference comparator 46 may then generate the first comparison signal 48 (e.g., either logical "high" or logical "low") based on whether the calibration output voltage 50 has exceeded the reference voltage 52.

If the calibration output voltage 50 has not exceeded the reference voltage 52, the illustrated reference comparator 46 outputs a logical "high" and causes the counter 54 to increment the counter value (e.g., "Count") that is provided to the DAC 41 in the transmit circuit 18. Incrementing the counter value may therefore increase the operating current (e.g., "Iled") of the light source 36. The increase in operating current may in turn increase the amount of light generated by the light source 36 and the amount of light received by the photodetector 32. When the calibration output voltage 50 exceeds the reference voltage 52, the illustrated reference comparator 46 outputs a logical "low" and the illustrated logic gate 58 generates a completion notification (e.g., "Cal_done"). Meanwhile, the DAC 41 may maintain the operational current of the light source 36 at the minimum value the caused the calibration output voltage 50 to exceed the reference voltage 52 due to the counter value programmed into the DAC 41. The illustrated phase 42 therefore provides closed loop control over the calibration output voltage 50 without modifying the gain of the TIA 34. The operational current of the light source 36 may optionally be decremented via a dual-loop control (not shown).

In one example, a bidirectional bus 69 may be coupled to the counter 54, the DAC 41 and a CPU (central processing unit, host processor, not shown). In such a case, the count value may be sent to the CPU as well as reset by the CPU, depending on the circumstances. The calibration circuit 22 may also include a saturation comparator 64 coupled to TIA 34, wherein the saturation comparator 64 generates a second comparison signal 66 (e.g., "tia_satb") based on the calibration output voltage 50 of the receive circuit 20 and a saturation voltage 68. The saturation voltage 68 may also be provided by the resistor ladder 62. In this regard, the resistor ladder 62 may be implemented in on-chip resistors that produce voltages at a relatively high accuracy.

Figure 4:
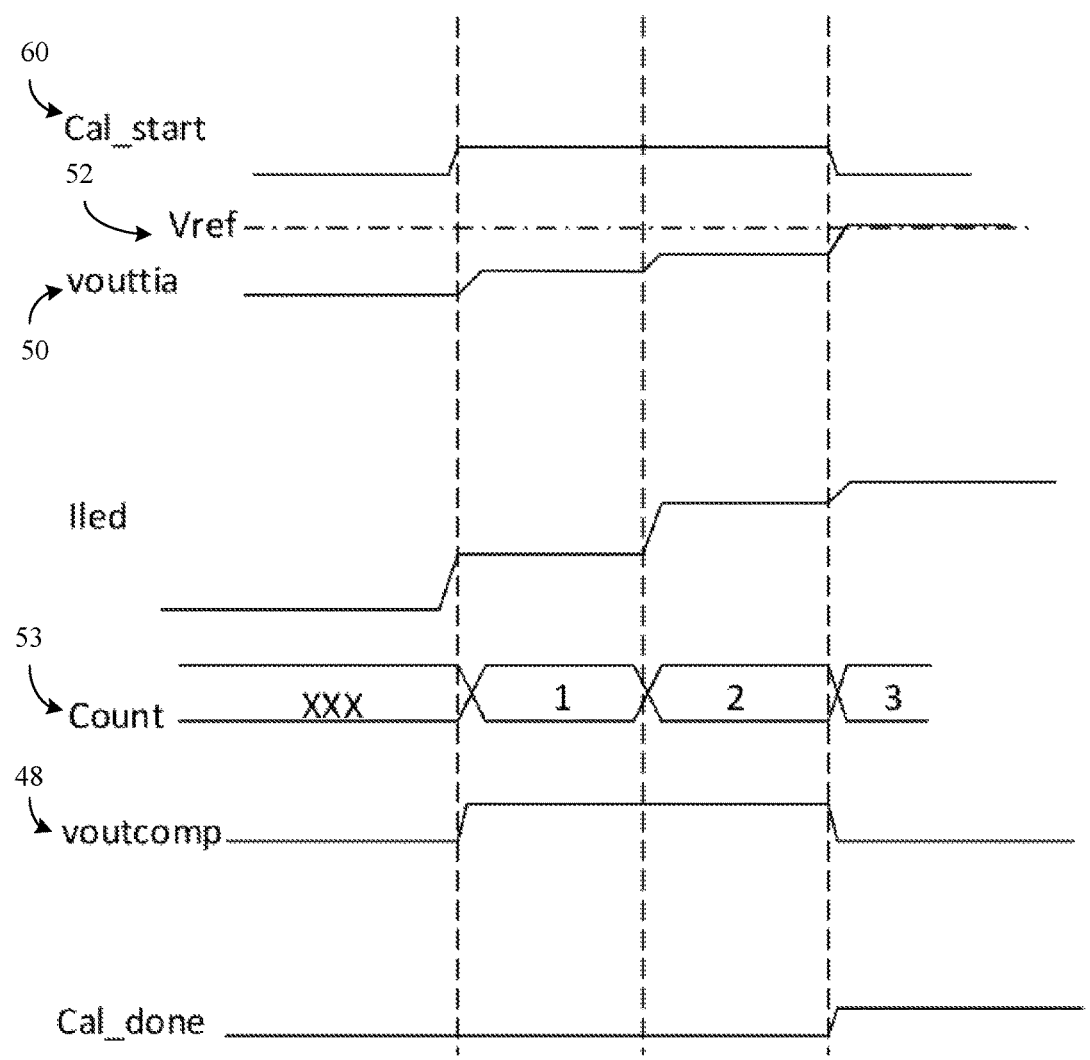
FIG. 4 is a signaling diagram of an example of a transmit and receive circuit calibration according to an embodiment.

FIG. 4 shows an example of the signaling waveforms for an example in which three increments of a counter value 53 provide an operating current for the light source that drives the calibration output voltage 50 above the reference voltage 52. Once the target output voltage of the receive circuit is achieved, the calibration completion notification is generated (e.g., "Cal-done" assertion), in the illustrated example.

Figure 5:
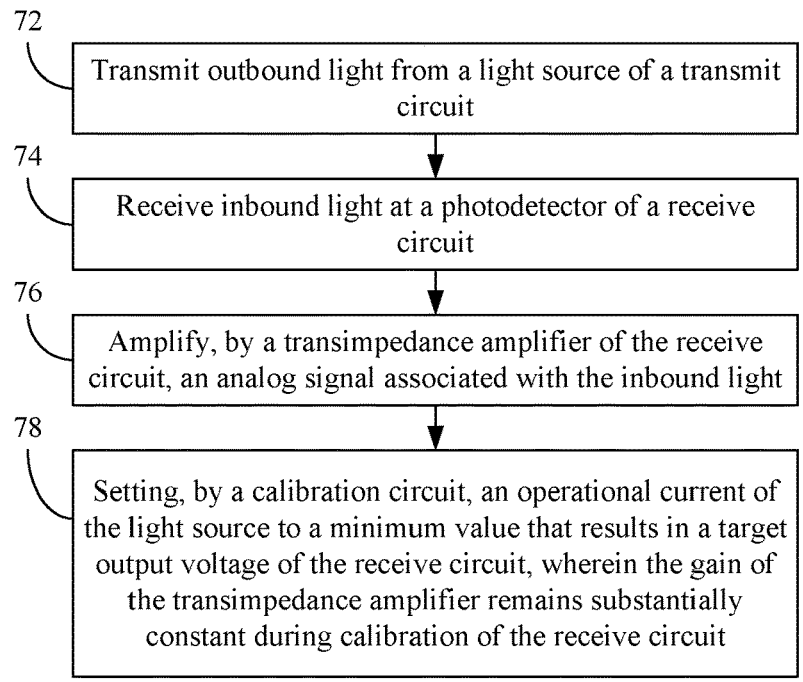
FIG. 5 is a flowchart of an example of a method of operating a measurement apparatus according to an embodiment.

FIG. 5 shows a method 70 of operating a measurement apparatus. The method 70 may generally be implemented in a health monitor system such as, for example, the system 10 (FIG. 1), already discussed. More particularly, the method 70 may be implemented in one or more modules as a set of logic instructions stored in a machine- or computer-readable storage medium such as random access memory (RAM), read only memory (ROM), programmable ROM (PROM), firmware, flash memory, etc., in configurable logic such as, for example, programmable logic arrays (PLAs), field programmable gate arrays (FPGAs), complex programmable logic devices (CPLDs), in fixed-functionality logic hardware using circuit technology such as, for example, application specific integrated circuit (ASIC), complementary metal oxide semiconductor (CMOS) or transistor-transistor logic (TTL) technology, or any combination thereof.

Illustrated processing block 72 provides for transmitting outbound light from a light source (e.g. LED) of a transmit circuit, wherein inbound light may be received at a photodetector of a receive circuit at block 74. Additionally, block 76 may amplify, by a transimpedance amplifier (TIA) of the receive circuit, an analog signal associated with the inbound light. Illustrated block 78 sets, by a calibration circuit, an operational current of the light source to a minimum value that results in a target output voltage of the receive circuit. Moreover, the gain of the transimpedance amplifier may remain substantially constant during calibrtation of the receive circuit. In one example, block 78 includes generating, by a reference comparator, a comparison signal based on a calibration output voltage of the receive circuit and a reference voltage and generating, by a counter, a counter value based on the comparison signal. In such a case, block 78 may also provide for maintaining, by a digital to analog converter of the transmit circuit, the operational current of the light source at the minimum value based on the counter value from the calibration circuit.

Figure 6:
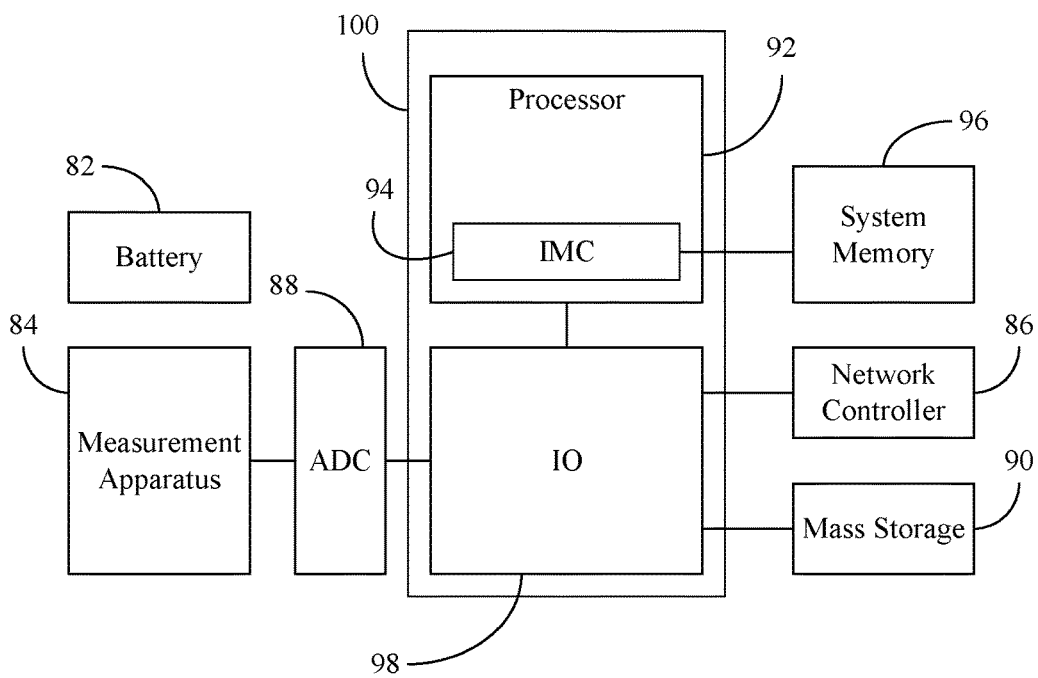
FIG. 6 is a block diagram of an example of a health monitor system according to an embodiment.

FIG. 6 shows a health monitor system 80 that may be readily substituted for the system 10 (FIG. 1), already discussed. In the illustrated example, the system 80 includes a battery 82 to supply power to the system 80, a measurement apparatus 84 (e.g., analog circuit), an analog to digital converter (ADC) 88, a network controller 86 (e.g., Bluetooth, Wi-Fi) and mass storage 90. The system 80 may also include a host processor 92 (e.g., CPU) having an integrated memory controller (IMC) 94, which may communicate with system memory 96. The system memory 96 may include, for example, dynamic random access memory (DRAM) configured as one or more memory modules such as, for example, dual inline memory modules (DIMMs), small outline DIMMs (SODIMMs), etc. The illustrated system 80 also includes an input output (IO) module 98 implemented together with the processor 92 on a semiconductor die 100 as a system on chip (SoC), wherein the IO module 98 functions as a host device and may communicate with, for example, the network controller 86, the mass storage 90, the measurement apparatus 84 via the ADC 88, and so forth.

The measurement apparatus 84 may generally be used to take PPG and PO measurements. More particularly, the measurement apparatus 84 may include, for example, the calibration phases 24, 42 (FIGS. 2 and 3, respectively). Accordingly, the apparatus 84 may include a transmit circuit including a light source and a receive circuit including a photodetector and a transimpedance amplifier (TIA) coupled to the photodetector. Moreover, the apparatus 84 may include a calibration circuit coupled to the transmit circuit and the receive circuit, wherein the calibration circuit includes a current controller to set an operational current of the light source to a minimum value that results in a target output voltage of the receive circuit. As already noted, the gain of the TIA may remain substantially constant and the ADC 88 may be deactivated during calibration of the receive circuit. Accordingly, the measurement apparatus 84 may substantially reduce delay and decrease power consumption.

Additional Notes and Examples:

Example 1 may include a measurement apparatus comprising a transmit circuit including a light source, a receive circuit including a photodetector and a transimpedance amplifier coupled to the photodetector, and a calibration circuit coupled to the transmit circuit and the receive circuit, the calibration circuit including a current controller to set an operational current of the light source to a minimum value that results in a target output voltage of the receive circuit, the current controller comprising a reference comparator to generate a first comparison signal based on a calibration output voltage of the receive circuit and a reference voltage, the current controller further comprising a counter coupled to the reference comparator, the counter to generate a counter value based on the first comparison signal, a local oscillator coupled to the counter, and a logic gate coupled to the reference comparator, the logic gate to generate a completion notification in response to the calibration output voltage of the receive circuit exceeding the reference voltage, wherein a gain of the transimpedance amplifier is to remain substantially constant during calibration of the receive circuit.

Example 2 may include the apparatus of Example 1, wherein the calibration circuit further includes a saturation comparator to generate a second comparison signal based on the calibration output voltage of the receive circuit and a saturation voltage.

Example 3 may include the apparatus of Example 2, further including a resistor ladder to provide the reference voltage and the saturation voltage.

Example 4 may include the apparatus of any one of Examples 1 to 3, wherein the transmit circuit further includes a switch coupled to the light source, a ground resistor coupled to the switch, and a digital to analog converter (DAC) coupled to the switch and the calibration circuit, the DAC to maintain the operational current of the light source at the minimum value based on the counter value from the calibration circuit.

Example 5 may include a health monitor system comprising a housing including a wearable form factor, an analog to digital converter (ADC), a low pass filter (LPF) coupled to the ADC, a transmit circuit including a light source, a receive circuit coupled to the LPF, the receive circuit including a photodetector and a transimpedance amplifier coupled to the photodetector, and a calibration circuit coupled to the transmit circuit and the receive circuit, the calibration circuit including a current controller to set an operational current of the light source to a minimum value that results in a target output voltage of the receive circuit, wherein a gain of the transimpedance amplifier is to remain substantially constant and the ADC is to be deactivated during calibration of the receive circuit.

Example 6 may include the system of Example 5, wherein the current controller includes a reference comparator to generate a first comparison signal based on a calibration output voltage of the receive circuit and a reference voltage, and a counter coupled to the reference comparator, the counter to generate a counter value based on the first comparison signal.

Example 7 may include the system of Example 6, wherein the calibration circuit further includes a local oscillator coupled to the counter.

Example 8 may include the system of Example 6, wherein the calibration circuit further includes a logic gate coupled to the reference comparator, the logic gate to generate a completion notification in response to the calibration output voltage of the receive circuit exceeding the reference voltage.

Example 9 may include the system of Example 6, wherein the calibration circuit further includes a saturation comparator to generate a second comparison signal based on the calibration output voltage of the receive circuit and a saturation voltage.

Example 10 may include the system of Example 9, further including a resistor ladder to provide the reference voltage and the saturation voltage.

Example 11 may include the system of any one of Examples 5 to 10, wherein the transmit circuit further includes a switch coupled to the light source, a ground resistor coupled to the switch, and a digital to analog converter (DAC) coupled to the switch and the calibration circuit, the DAC to maintain the operational current of the light source at the minimum value based on a counter value from the calibration circuit.

Example 12 may include a measurement apparatus comprising a transmit circuit including a light source, a receive circuit including a photodetector and a transimpedance amplifier coupled to the photodetector, and a calibration circuit coupled to the transmit circuit and the receive circuit, the calibration circuit including a current controller to set an operational current of the light source to a minimum value that results in a target output voltage of the receive circuit, wherein a gain of the transimpedance amplifier is to remain substantially constant during calibration of the receive circuit.

Example 13 may include the apparatus of Example 12, wherein the current controller includes a reference comparator to generate a first comparison signal based on a calibration output voltage of the receive circuit and a reference voltage, and a counter coupled to the reference comparator, the counter to generate a counter value based on the first comparison signal.

Example 14 may include the apparatus of Example 13, wherein the calibration circuit further includes a local oscillator coupled to the counter.

Example 15 may include the apparatus of Example 13, wherein the calibration circuit further includes a logic gate coupled to the reference comparator, the logic gate to generate a completion notification in response to the calibration output voltage of the receive circuit exceeding the reference voltage.

Example 16 may include the apparatus of Example 13, wherein the calibration circuit further includes a saturation comparator to generate a second comparison signal based on the calibration output voltage of the receive circuit and a saturation voltage.

Example 17 may include the apparatus of Example 16, further including a resistor ladder to provide the reference voltage and the saturation voltage.

Example 18 may include the apparatus of any one of Examples 11 to 17, wherein the transmit circuit further includes a switch coupled to the light source, a ground resistor coupled to the switch, and a digital to analog converter (DAC) coupled to the switch and the calibration circuit, the DAC to maintain the operational current of the light source at the minimum value based on a counter value from the calibration circuit.

Example 19 may include a method of operating a measurement apparatus comprising transmitting outbound light from a light source of a transmit circuit, receiving inbound light at a photodetector of a receive circuit, amplifying, by a transimpedance amplifier of the receive circuit, an analog signal associated with the inbound light, and setting, by a calibration circuit, an operational current of the light source to a minimum value that results in a target output voltage of the receive circuit, wherein the gain of the transimpedance amplifier remains substantially constant during calibration of the receive circuit.

Example 20 may include the method of Example 19, further including generating, by a reference comparator, a comparison signal based on a calibration output voltage of the receive circuit and a reference voltage, and generating, by a counter, a counter value based on the comparison signal.

Example 21 may include the method of Example 20, further including providing a clock signal from a local oscillator to the counter.

Example 22 may include the method of Example 20, further including generating, by a logic gate, a completion notification in response to the calibration output voltage of the receive circuit exceeding the reference voltage.

Example 23 may include the method of Example 20, further including generating, by a saturation comparator, a second comparison signal based on the calibration output voltage of the receive circuit and the saturation voltage.

Example 24 may include the method of any one of Examples 20 to 23, further including maintaining, by a digital to analog converter of the transmit circuit, the operational current of the light source at the minimum value based on a counter value from the calibration circuit.

Example 25 may include a measurement apparatus comprising means for transmitting outbound light from a light source of a transmit circuit, means for receiving inbound light at a photodetector of a receive circuit, means for amplifying, by a transimpedance amplifier of the receive circuit, an analog signal associated with the inbound light, means for setting, by a calibration circuit, an operational current of the light source to a minimum value that results in a target output voltage of the receive circuit, wherein the gain of the transimpedance amplifier is to remain substantially constant during calibration of the receive circuit.

Example 26 may include the apparatus of Example 25, further including means for generating, by a reference comparator, a comparison signal based on a calibration output voltage of the receive circuit and a reference voltage, and means for generating, by a counter, a counter value based on the comparison signal.

Example 27 may include the apparatus of Example 26, further including means for providing a clock signal from a local oscillator to the counter.

Example 28 may include the apparatus of Example 26, further including means for generating, by a logic gate, a completion notification in response to the calibration output voltage of the receive circuit exceeding the reference voltage.

Example 29 may include the apparatus of Example 26, further including means for generating, by a saturation comparator, a second comparison signal based on the calibration output voltage of the receive circuit and the saturation voltage.

Example 30 may include the apparatus of any one of Examples 26 to 29, further including means for maintaining, by a digital to analog converter of the transmit circuit, the operational current of the light source at the minimum value based on a counter value from the calibration circuit.

Techniques described herein may therefore reduce delay and power consumption. More particularly, a simple receive circuit/chain may set the LED operating current (e.g., based on the signal strength on the analog side) and eliminate ADC and/or processor power consumption during calibration. The power savings may be significant. For example, switching the LED current at 40 mA may result in an average current of 2.4 mA for a 100 Hz measurement cycle. Compared to a conventional solution that drives the LED at, for example, a 150 mA for an average current of 3.5 mA, a 31.43% savings may be achieved (for the same 100 Hz measurement cycle).

Embodiments are applicable for use with all types of semiconductor integrated circuit ("IC") chips. Examples of these IC chips include but are not limited to processors, controllers, chipset components, programmable logic arrays (PLAs), memory chips, network chips, systems on chip (SoCs), SSD/NAND controller ASICs, and the like. In addition, in some of the drawings, signal conductor lines are represented with lines. Some may be different, to indicate more constituent signal paths, have a number label, to indicate a number of constituent signal paths, and/or have arrows at one or more ends, to indicate primary information flow direction. This, however, should not be construed in a limiting manner. Rather, such added detail may be used in connection with one or more exemplary embodiments to facilitate easier understanding of a circuit. Any represented signal lines, whether or not having additional information, may actually comprise one or more signals that may travel in multiple directions and may be implemented with any suitable type of signal scheme, e.g., digital or analog lines implemented with differential pairs, optical fiber lines, and/or single-ended lines.

Example sizes/models/values/ranges may have been given, although embodiments are not limited to the same. As manufacturing techniques (e.g., photolithography) mature over time, it is expected that devices of smaller size could be manufactured. In addition, well known power/ground connections to IC chips and other components may or may not be shown within the figures, for simplicity of illustration and discussion, and so as not to obscure certain aspects of the embodiments. Further, arrangements may be shown in block diagram form in order to avoid obscuring embodiments, and also in view of the fact that specifics with respect to implementation of such block diagram arrangements are highly dependent upon the platform within which the embodiment is to be implemented, i.e., such specifics should be well within purview of one skilled in the art. Where specific details (e.g., circuits) are set forth in order to describe example embodiments, it should be apparent to one skilled in the art that embodiments can be practiced without, or with variation of, these specific details. The description is thus to be regarded as illustrative instead of limiting.

The term "coupled" may be used herein to refer to any type of relationship, direct or indirect, between the components in question, and may apply to electrical, mechanical, fluid, optical, electromagnetic, electromechanical or other connections. In addition, the terms "first", "second", etc. may be used herein only to facilitate discussion, and carry no particular temporal or chronological significance unless otherwise indicated.

Those skilled in the art will appreciate from the foregoing description that the broad techniques of the embodiments can be implemented in a variety of forms. Therefore, while the embodiments have been described in connection with particular examples thereof, the true scope of the embodiments should not be so limited since other modifications will become apparent to the skilled practitioner upon a study of the drawings, specification, and following claims.

We claim:

1. An apparatus comprising:
   a transmit circuit including a light source;
   a receive circuit including a photodetector and a transimpedance amplifier coupled to the photodetector; and
   a calibration circuit coupled to the transmit circuit and the receive circuit, the calibration circuit including,
       a current controller to set an operational current of the light source to a minimum value that results in a target output voltage of the receive circuit, the current controller comprising a reference comparator to generate a first comparison signal based on a calibration output voltage of the receive circuit and a reference voltage, the current controller further comprising a counter coupled to the reference comparator, the counter to generate a counter value based on the first comparison signal,
       a local oscillator coupled to the counter, and
       a logic gate coupled to the reference comparator, the logic gate to generate a completion notification in response to the calibration output voltage of the receive circuit exceeding the reference voltage, wherein a gain of the transimpedance amplifier is to remain substantially constant during calibration of the receive circuit.

2. The apparatus of claim 1, wherein the calibration circuit further includes a saturation comparator to generate a second comparison signal based on the calibration output voltage of the receive circuit and a saturation voltage.

3. The apparatus of claim 2, further including a resistor ladder to provide the reference voltage and the saturation voltage.

4. The apparatus of claim 1, wherein the transmit circuit further includes:
   a switch coupled to the light source;
   a ground resistor coupled to the switch; and
   a digital to analog converter (DAC) coupled to the switch and the calibration circuit, the DAC to maintain the operational current of the light source at the minimum value based on the counter value from the calibration circuit.

5. An apparatus comprising:
   a transmit circuit including a light source;
   a receive circuit including a photodetector and a transimpedance amplifier coupled to the photodetector; and
   a calibration circuit coupled to the transmit circuit and the receive circuit, the calibration circuit including:
      a current controller to set an operational current of the light source to a minimum value that results in a target output voltage of the receive circuit, wherein a gain of the transimpedance amplifier is to remain substantially constant during calibration of the receive circuit, the current controller including:
         a reference comparator to generate a first comparison signal based on a calibration output voltage of the receive circuit and a reference voltage, and
         a counter coupled to the reference comparator, the counter to generate a counter value based on the first comparison signal; and
      a logic gate coupled to the reference comparator, the logic gate to generate a completion notification in response to the calibration output voltage of the receive circuit exceeding the reference voltage.

6. The apparatus of claim 5, wherein the calibration circuit further includes a local oscillator coupled to the counter.

7. The apparatus of claim 5, wherein the calibration circuit further includes a saturation comparator to generate a second comparison signal based on the calibration output voltage of the receive circuit and a saturation voltage.

8. The apparatus of claim 7, further including a resistor ladder to provide the reference voltage and the saturation voltage.

9. The apparatus of claim 5, wherein the transmit circuit further includes:
   a switch coupled to the light source;
   a ground resistor coupled to the switch; and
   a digital to analog converter (DAC) coupled to the switch and the calibration circuit, the DAC to maintain the operational current of the light source at the minimum value based on a counter value from the calibration circuit.

10. A method comprising:
    transmitting outbound light from a light source of a transmit circuit;
    receiving inbound light at a photodetector of a receive circuit;
    amplifying, by a transimpedance amplifier of the receive circuit, an analog signal associated with the inbound light;
    generating, by a reference comparator, a comparison signal based on a calibration output voltage of the receive circuit and a reference voltage;
    generating, by a counter, a counter value based on the comparison signal;
    generating, by a logic gate, a completion notification in response to the calibration output voltage of the receive circuit exceeding the reference voltage; and
    setting, by a calibration circuit, an operational current of the light source to a minimum value that results in a target output voltage of the receive circuit, wherein the gain of the transimpedance amplifier remains substantially constant during calibration of the receive circuit.

11. The method of claim 10, further including providing a clock signal from a local oscillator to the counter.

12. The method of claim 10, further including generating, by a saturation comparator, a second comparison signal based on the calibration output voltage of the receive circuit and a saturation voltage.

13. The method of claim 10, further including maintaining, by a digital to analog converter of the transmit circuit, the operational current of the light source at the minimum value based on a counter value from the calibration circuit.

* * * * *